(12) United States Patent
Dunwoody et al.

(10) Patent No.: US 8,865,227 B2
(45) Date of Patent: Oct. 21, 2014

(54) METAL CARBONATE PARTICLES AND METHODS OF MAKING THEREOF

(75) Inventors: Nicholas Dunwoody, Chester, NH (US); Zachary S. Wilson, Quincy, MA (US)

(73) Assignee: Smith & Nephew (Overseas) Limited, London (GB)

( * ) Notice: Subject to any disclaimer, the term of this patent is extended or adjusted under 35 U.S.C. 154(b) by 1022 days.

(21) Appl. No.: 12/333,585

(22) Filed: Dec. 12, 2008

(65) Prior Publication Data

US 2009/0162448 A1 Jun. 25, 2009

Related U.S. Application Data

(60) Provisional application No. 61/015,223, filed on Dec. 20, 2007.

(51) Int. Cl.
| | | |
|---|---|---|
| *A61K 9/14* | (2006.01) | |
| *A61K 33/24* | (2006.01) | |
| *A61K 33/38* | (2006.01) | |
| *C09C 1/00* | (2006.01) | |
| *C01G 5/00* | (2006.01) | |
| *C09C 3/06* | (2006.01) | |
| *A61K 33/10* | (2006.01) | |
| *C09C 3/08* | (2006.01) | |
| *C01B 31/24* | (2006.01) | |

(52) U.S. Cl.
CPC . *A61K 33/10* (2013.01); *C09C 1/00* (2013.01); *C01P 2004/02* (2013.01); *C01P 2002/72* (2013.01); *C01P 2004/62* (2013.01); *C01G 5/00* (2013.01); *C09C 3/063* (2013.01); *C09C 3/08* (2013.01); *C01B 31/24* (2013.01); *C01P 2004/50* (2013.01); *A61K 33/38* (2013.01)
USPC ........... 424/617; 424/489; 424/490; 424/618; 424/715

(58) Field of Classification Search
None
See application file for complete search history.

(56) References Cited

U.S. PATENT DOCUMENTS

| | | | |
|---|---|---|---|
| 4,749,572 A | 6/1988 | Ahari | |
| 4,803,066 A | 2/1989 | Edwards | |
| 4,828,832 A | 5/1989 | De Cuellar et al. | |
| 4,847,049 A | 7/1989 | Yamamoto | |
| 4,908,355 A | 3/1990 | Gettings et al. | |
| 4,952,411 A | 8/1990 | Fox, Jr. et al. | |
| 4,980,172 A | 12/1990 | Fey | |
| 5,122,418 A | 6/1992 | Nakane et al. | |
| 5,143,717 A | 9/1992 | Davis | |
| 5,270,358 A | 12/1993 | Asmus | |
| 5,369,155 A | 11/1994 | Asmus | |
| 5,374,432 A | 12/1994 | Fox et al. | |
| 5,429,761 A * | 7/1995 | Havelka et al. | ................ 252/74 |
| 5,454,886 A | 10/1995 | Burrell et al. | |
| 5,681,575 A | 10/1997 | Burrell et al. | |
| 5,744,151 A | 4/1998 | Capelli | |
| 5,753,251 A | 5/1998 | Burrell et al. | |
| 5,770,255 A | 6/1998 | Burrell et al. | |
| 5,792,793 A | 8/1998 | Oda et al. | |
| 5,811,463 A | 9/1998 | Legzdins et al. | |
| 5,837,275 A | 11/1998 | Burrell et al. | |
| 5,848,995 A | 12/1998 | Walder | |
| 5,945,032 A | 8/1999 | Breitenbach et al. | |
| 5,958,440 A | 9/1999 | Burrell et al. | |
| 5,985,308 A | 11/1999 | Burrell et al. | |
| 6,017,553 A | 1/2000 | Burrell et al. | |
| 6,022,547 A | 2/2000 | Herb et al. | |
| 6,071,541 A | 6/2000 | Murad | |
| 6,071,543 A | 6/2000 | Thornfeldt | |
| 6,123,925 A | 9/2000 | Barry et al. | |
| 6,126,931 A | 10/2000 | Sawan et al. | |
| 6,187,290 B1 | 2/2001 | Gilchrist et al. | |
| 6,197,351 B1 | 3/2001 | Neuwirth | |
| 6,201,164 B1 | 3/2001 | Wulff et al. | |
| 6,224,898 B1 | 5/2001 | Balogh et al. | |
| 6,238,686 B1 | 5/2001 | Burrell et al. | |
| 6,258,385 B1 | 7/2001 | Antelman | |
| 6,277,169 B1 | 8/2001 | Hampden-Smith et al. | |
| 6,294,186 B1 | 9/2001 | Beerse et al. | |
| 6,333,093 B1 | 12/2001 | Burrell et al. | |
| 6,454,754 B1 | 9/2002 | Frank | |
| 6,692,773 B2 | 2/2004 | Burrell et al. | |
| 6,720,006 B2 | 4/2004 | Hanke et al. | |
| 6,899,903 B2 | 5/2005 | Quillin | |
| 6,939,568 B2 | 9/2005 | Burrell et al. | |
| 6,989,157 B2 | 1/2006 | Gillis et al. | |
| 7,087,249 B2 | 8/2006 | Burrell et al. | |
| 7,201,888 B2 | 4/2007 | Berube et al. | |
| 7,799,425 B2 * | 9/2010 | Chikamori et al. | ........... 428/403 |

(Continued)

FOREIGN PATENT DOCUMENTS

| | | |
|---|---|---|
| CN | 1082645 | 2/1994 |
| CN | 1236620 | 12/1999 |
| CN | 1241662 | 1/2000 |
| CN | 1262093 | 8/2000 |
| CN | 1279222 | 1/2001 |
| CN | 1291666 | 4/2001 |
| CN | 1291667 | 4/2001 |
| CN | 1306117 | 8/2001 |
| CN | 1322474 | 11/2001 |
| CN | 1322874 | 11/2001 |

(Continued)

OTHER PUBLICATIONS

Goel et al., Effect of PVP, PVA and POLE surfactants on the size of iridium nanoparticles, Open Journal of Inorganic Chemistry (2012), vol. 2, pp. 67-73.*

(Continued)

*Primary Examiner* — Abigail Fisher

*Assistant Examiner* — Frank Choi

(74) *Attorney, Agent, or Firm* — Fish & Richardson P.C.

(57) ABSTRACT

Silver-containing particles, and methods of making silver-containing particles are disclosed.

21 Claims, 9 Drawing Sheets

(56) References Cited

U.S. PATENT DOCUMENTS

| | | |
|---|---|---|
| 2002/0001628 A1 | 1/2002 | Ito |
| 2002/0025344 A1 | 2/2002 | Newman et al. |
| 2002/0051824 A1 | 5/2002 | Burrell et al. |
| 2002/0192298 A1 | 12/2002 | Burrell et al. |
| 2003/0021854 A1 | 1/2003 | Burrell et al. |
| 2003/0170314 A1 | 9/2003 | Burrell et al. |
| 2004/0009964 A1 | 1/2004 | Capelli |
| 2004/0176312 A1 | 9/2004 | Gillis |
| 2004/0197884 A1* | 10/2004 | Okuda et al. .......... 435/174 |
| 2005/0100621 A1 | 5/2005 | Popp et al. |
| 2008/0014247 A1 | 1/2008 | Bhol et al. |
| 2008/0014278 A1 | 1/2008 | Chen et al. |
| 2008/0044491 A1 | 2/2008 | Lyczak et al. |
| 2008/0050452 A1 | 2/2008 | Chen et al. |

FOREIGN PATENT DOCUMENTS

| | | |
|---|---|---|
| CN | 1328819 | 1/2002 |
| CN | 1328827 | 1/2002 |
| DE | 517935 | 1/1931 |
| DE | 2200723 A | 1/1972 |
| DE | 19541735 A1 | 5/1997 |
| EP | 0136768 A2 | 4/1985 |
| EP | 0254413 | 1/1988 |
| EP | 0356060 | 7/1989 |
| EP | 0328421 A2 | 8/1989 |
| EP | 0355009 A1 | 2/1990 |
| EP | 0378147 A2 | 7/1990 |
| EP | 0599188 A1 | 6/1994 |
| EP | 0681841 A1 | 11/1995 |
| EP | 0439513 | 3/1996 |
| EP | 1 716 947 | 11/2006 |
| EP | 1716947 | 11/2006 |
| EP | 1 849 464 | 10/2007 |
| EP | 1849464 | 10/2007 |
| GB | 420052 | 11/1934 |
| GB | 427106 | 4/1935 |
| GB | 965010 | 7/1964 |
| GB | 1270410 | 4/1972 |
| GB | 2140684 | 12/1984 |
| HU | 9800078 A | 9/1999 |
| IL | 74641 A1 | 5/1988 |
| IT | 022309 | 12/1990 |
| JP | 11060493 | 3/1999 |
| JP | 11116488 A | 4/1999 |
| JP | 11124335 A | 5/1999 |
| JP | 2000 327578 | 11/2000 |
| JP | 04244029 A | 9/2002 |
| RU | 2042352 | 9/1995 |
| WO | WO8909054 A | 10/1989 |
| WO | WO9323092 | 11/1993 |
| WO | WO9513704 A | 5/1995 |
| WO | WO9617595 | 6/1996 |
| WO | WO9822116 | 5/1998 |
| WO | WO9841095 A | 9/1998 |
| WO | WO9851273 | 11/1998 |
| WO | WO9908691 | 2/1999 |
| WO | WO9960999 | 12/1999 |
| WO | WO0027390 A | 5/2000 |
| WO | WO0030697 | 6/2000 |
| WO | WO0078281 A1 | 12/2000 |
| WO | WO0078282 A1 | 12/2000 |
| WO | WO0124839 A1 | 4/2001 |
| WO | WO0126627 A1 | 4/2001 |
| WO | WO0141774 A1 | 6/2001 |
| WO | WO0141819 | 6/2001 |
| WO | WO0143788 A2 | 6/2001 |
| WO | WO0149115 A1 | 7/2001 |
| WO | WO0149301 A1 | 7/2001 |
| WO | WO0149302 A1 | 7/2001 |
| WO | WO0149303 A1 | 7/2001 |
| WO | WO0115710 A2 | 8/2001 |
| WO | WO0168179 A1 | 9/2001 |
| WO | WO0180920 | 9/2001 |
| WO | WO0174300 A1 | 10/2001 |
| WO | WO 02/02059 | 1/2002 |
| WO | WO 02/09729 | 2/2002 |
| WO | WO0209729 A2 | 2/2002 |
| WO | WO0215698 | 2/2002 |
| WO | WO0218699 A1 | 3/2002 |
| WO | WO0285299 A2 | 10/2002 |
| WO | WO02085384 A2 | 10/2002 |
| WO | WO02085385 | 10/2002 |
| WO | WO02085386 | 10/2002 |
| WO | WO02085387 A2 | 10/2002 |
| WO | WO 2004/037187 | 5/2004 |
| WO | WO 2005/074949 | 8/2005 |
| WO | WO 2005075132 A1 * | 8/2005 |
| WO | WO 2006/105362 | 10/2006 |
| WO | WO 2008/005705 | 1/2008 |

OTHER PUBLICATIONS

The Merck Index, 13$^{th}$ Edition, pp. 1525-1526, 2001.
Berger et al., "Electrically Generated Silver Ions: Quantitative Effects on Bacterial and Mammalian Cells," *Antimicrobial Agents and Chemotherapy* 9(2):357-358 (1976).
Borm et al., "Toxicological Hazards of Inhaled Nanoparticles—Potential Implications for Drug Delivery," *Journal of Nanoscience and Nanotechnology* 4(5):521-531 (2004).
Burrell et al., "Efficacy of Silver-Coated Dressings as Bacterial Barriers in a Rodent Burn Sepsis Model", *Wounds* 11(4):64-71 (1999).
Chemical Abstracts 25:2814a (1931).
Chemical Abstracts 111:127029 (1989).
Davis et al., "Effects of Microamperage, Medium and Bacterial Concentration on Iontophoric Killing in of Bacteria in Fluid," *Antimicrobial Agents and Chemotherapy* 33(4):442-447 (1989).
Demling et al., "The Role of Silver in Wound Healing: Effects of Silver on Wound Management," *Wounds* 13(1):5-15 (2001).
Derwent Abstract, accession No. 1994-089981; abstracting RU 2003335 (Nov. 1993).
Djokic et al., "An Electrochemical Analysis of Thin Silver Films Produced by Reactive Sputtering," *J. Electrochem Society* 148(3):191-196 (2001).
Falcone et al., "Inhibitory Effects of Electrically Activated Silver Material on Cutaneous Wound Bacteria," *Plastic and Reconstructive Surgery* 77(3):455-458 (1986).
Fischer et al., "Colloidal Gold Dragees," *WPIDS Abstract* 1966-11488F (1966).
Grier, "Silver and Its Compounds," *Disinfection, Sterlization and Preservation*, Block (ed), Lea & Febiger, 2$^{nd}$ ed., pp. 395-407 (1977).
Hall et al., "Inhibitory and Cidal Antimicrobial Actions of Electrically Generated Silver Ions," *Journal of Oral Maxillofacial Surgery* 45:779-784 (1987).
Harada, "Topical Therapeutic Cream Contains Subcutaneous Horse Fat and Edible Gold Flakes for Activating Blood Circulation," *WPIDS Abstract* 1989-312257 (1989).
HCAPLUS Abstract, accession No. 1995:331180 (1995).
HCAPLUS Abstract, accession No. 2001:926257 (2001).
HCAPLUS Abstract, accession No. 2005:332256 (2005).
HCAPLUS Abstract, accession No. 2006:751751 (2006).
Hoet et al., "Nanoparticles—Known and Unknown Health Risks," *Journal of Nanbiotechnology* 2(12):1-15 (2004).
Kirsner et al., "The Role of Silver in Wound Healing: Matrix Metalloproteinases in Normal and Impared Wound Healing: A Potential Role for Nanocrystalline Silver," *Wounds* 13(3):5-12 (2001).
Medline abstract 83209466 (1983).
Medline abstract 88076157 (1988).
Medline abstract 1998454009 (1999).
Norby et al., "Decomposition of Silver Carbonate; the Crystal Structure of Two High-Temperature Modifications of $Ag_2CO_3$," *Inorg. Chem.*, 41(14):3628-3637, 2002.
Olson et al., "Healing of Porcine Donor Sites Covered with Silver-Coated Dressings," *Eur. J. Surg.* 166:486-489 (2000).
Ovington, "The Role of Silver in Wound Healing: Why is Nanocrystalline Silver Superior?," *Wounds* 13(2):5-10 (2001).

(56) References Cited

OTHER PUBLICATIONS

Ozkan, "Quantum Dots and Other Nanoparticles: What Can They Offer to Drug Discovery?," *Drug Discovery Today* 9(24):1065-1071 (2004).

Rodrigues et al., "Role of Lysosomes on Human Ulcerogenic Gastrophathies. Effect of Zinc Ion on the Lysosomal Stability," *Arquivos de Gastroenterologi* 35(4):247-251 (1998).

Sant et al., "Morphology of Novel Antimicrobial Silver Films Deposited by Magnetron Sputtering," *Scripta Materials* 41(12):1333-1339 (1999).

Sant et al., "Novel Duplex Antimicrobial Silver Films Deposited by Magnetron Sputtering," *Phil Mag. Let.* 80(4):249-256 (2000).

Silbermintz, A. et al., "Inflammatory Bowel Diseases," *Pediatrics Annals* 35(4):269-274 (Apr. 2006).

Souza, H. et al., "Apoptosis in the Intestinal Mucosa of Patients with Inflammatory Bowel Disease: evidence of altered expression of FasL and perforin cytotoxic pathways," *Int. J. Colorectal Dis.* 20:277-286 (2005).

Spadaro et al., "Antibacterial Effects of Silver Electrodes," *IEEE Eng. In Med. & Biol. Soc.*, pp. 215-218 (1981).

Thibodeau et al., "Inhibition and Killing of Oral Bacteria by Silver Ions Generated with Low Intensity Direct Current," *Journal of Dental Research* 57(9-10):922-926 (1978).

Thornton, "Coating Deposition by Sputtering," in Bunshah et al., *Deposition Technologies for Films and Coatings*, Noyes Publishing, New Jersey, pp. 170-243 (1982).

Thornton, "Influence of Apparatus Geometry and Deposition Conditions on the Structure and Topography of Thick Sputtered Coatings," *J. Vac. Sci. Technol.* 11(4):666-670 (1974).

Tredget, "Evaluation of Wound Healing Using Silver Dressing," (1996).

Tredget, "A Matched-Pair Randomized Study Evaluating the Efficacy and Safety of Acticoat Silver-Coated Dressing for the Treatment of Burn Wounds", *J. Burn Care & Rehab* 19:531-537 (1998).

Voigt et al., "The Use of Acticoat as Silver Impregnated Telfa Dressings in a Regional Burn and Wound Care Center: The Clinician's View," *Wounds* 13(2):11-20 (2001).

Williams, "Nanocrystallne Metals: Another Opportunity for Medical Devices?," *Medical Device Technology* 14(9):12 (2003).

Wright et al., "Wound Management in an Era of Increasing Bacterial Antibiotic Resistance: A Role for Topical Silver Treatment," *AJIC* 26(6):572-577 (1998).

Wright et al., "Efficacy of Topical Silver Against Fungal Burn Wound Pathogens," AJIC 27(4):344-358 (1999).

Wright et al., "Early Healing Events in a Porcine Model of Contaminated Wounds: Effects of Nanocrystalline Silver on Matrix Metalloproteinases, Cell Apoptosis, and Healing," *Wound Repair & Regen* 10:141-151 (2002).

Wright et al., "The Comparative Efficacy of Two Antimicrobial Barrier Dressings: In-vitro Examination of Two Controlled Release of Silver Dressings," *Wounds* 10(6):179-188 (1998).

Yin et al., "Effects of Acticoat Antimicrobial Barrier Dressing on Wound Healing and Graft Take," *J. Burn Care & Rehab* 2:s231 (1999).

Yin et al., "Comparative Evaluation of the Antimicrobial Activity of ACTICOAT Antimicrobial Barrier Dressing," *J. Burn Care & Rehab* 20(3):195-200 (1999).

Written Opinion and International Preliminary Report on Patentability for application No. PCT/US2008/086554, dated Jul. 1, 2010.

\* cited by examiner

METAL CARBONATE PARTICLES AND METHODS OF MAKING THEREOF

CROSS-REFERENCE TO RELATED APPLICATIONS

This application claims the benefit of the filing date of U.S. Provisional Patent Application Ser. No. 61/015,223, filed Dec. 20, 2007, the contents of which are hereby incorporated by reference.

TECHNICAL FIELD

This disclosure relates to metal carbonate particles, as well as related methods, compositions and articles.

BACKGROUND

Silver carbonate has been reported to be effective in treating some undesirable microbial conditions. Different methods have been developed to synthesize silver carbonate.

SUMMARY

This disclosure relates to metal carbonate particles, as well as related methods, compositions and articles.

In one aspect, the disclosure features a particle including more than 70 percent metal carbonate (e.g., silver carbonate) by weight. The particle has an average maximum dimension of less than 500 nanometers.

In another aspect, the disclosure features a method of making a particle. The method includes obtaining a mixture of at least one metal salt (e.g., silver salt), water, and a miscible organic solvent. The method also includes adding a base to the mixture to precipitate a metal oxide (e.g., silver oxide), and exposing the metal oxide to $CO_2$ to obtain a particle.

In another aspect, the disclosure features a method of making a particle. The method includes obtaining a mixture of at least one metal salt (e.g., silver salt) in an aqueous solution, exposing the mixture to a carbonate source, and precipitating the particle.

In a further aspect, the disclosure features a composition that includes a pharmaceutically acceptable carrier and at least one of the aforementioned particles in the pharmaceutically acceptable carrier.

In an additional aspect, the disclosure features a method of treating a subject having a condition, where the method includes exposing the subject to at least one of the aforementioned particles to treat the condition.

In another aspect, the disclosure features an article that includes at least one of the aforementioned particles.

Embodiments can include one or more of the following features.

In certain embodiments, the metal can be silver.

In some embodiments, the particle further includes the metal in elemental form. The particle can include a core-shell structure, such as a structure including a metal carbonate outer shell around a metal core. The particle can be free of fatty acids.

In some embodiments, the metal carbonate is nanocrystalline and/or atomically disordered. The particle can be antimicrobial and/or anti-inflammatory.

In some embodiments, exposing the metal oxide to $CO_2$ includes exposing the metal oxide to a flow of $CO_2$ gas.

In some embodiments, the base is sodium hydroxide. The metal salt can be metal nitrate. The miscible organic solvent can be tetrahydrofuran, acetone, and/or methanol. In some embodiments, the mixture of at least one metal salt, water, and a miscible organic solvent further includes a metal powder and/or one or more fatty acids. The fatty acids can include stearic acid and/or oleic acid. In some embodiments, the mixture of at least one metal salt in an aqueous solution further comprises a metal powder and/or a stabilizing polymer. The stabilizing polymer can include hydrolyzed polyvinyl alcohol. In some embodiments, the carbonate source is sodium carbonate.

In certain embodiments, an article containing at least one of the aforementioned particles can be in a form selected from creams, nanodispersions, solutions, powders, foams, gels, lotions, pastes, ointments, sprays, drops and suppositories.

In some embodiments, an article containing at least one of the aforementioned particles can be in a form selected from a microcapsule, a dressing, an implant, a wound closure, a suture, a staple, an adhesive, a mesh, a prosthetic device, a controlled drug delivery system, a wound covering or a filler.

Embodiments can include one or more of the following advantages.

In some embodiments, the metal carbonate particles are antimicrobial and/or anti-inflammatory. The particles can be amenable to a variety of formulations, such as creams, nanodispersions, solutions, powders, foams, gels, lotions, pastes, ointments, sprays, drops or suppositories. The particles can be easily delivered to a subject.

In some embodiments, the metal carbonate particles are stable, such that they do not agglomerate and/or decompose over a period of time (e.g., 30 days, 60 days, 90 days, 120 days, a year, or two years). The metal carbonate particles can be easily made in a short amount of time (e.g., two days, three days, or a week) and in bulk quantities (e.g., 100 grams, 500 grams, one kilo, five kilos, 10 kilos, 50 kilos, 100 kilos, or a ton). The metal carbonate particles can be suitable for use in a variety of settings, such as a household, a hospital, and/or an industrial setting. In some embodiments, the metal carbonate particles are cheap to synthesize.

Other features and advantages of the disclosure will be apparent from the description and drawings, and from the claims.

DETAILED DESCRIPTION

Metal-containing materials can be used to treat a subject with a condition by contacting an area of the subject having the condition with these materials. The metal-containing material can be in the form of metal carbonate particles.

As referred to herein, a particle has a maximum dimension of less than one micron (e.g., less than 750 nanometers, less than 500 nanometers, less than 250 nanometers, or less than 100 nanometers). In some embodiments, the particle has a maximum dimension of around 50 nanometers (e.g., around 100 nanometers, around 250 nanometers, around 500 nanometers, or around 750 nanometers). A collection of particles has a maximum average dimension of less than one micron (e.g., less than 750 nanometers, less than 500 nanometers, less than 250 nanometers, or less than 100 nanometers). In some embodiments, a collection of particles has a maximum average dimension of around 50 nanometers (e.g., around 100 nanometers, around 250 nanometers, around 500 nanometers, or around 750 nanometers). The range of maximum average size of a collection of particles can range from 20 nm to 500 nm (e.g., from 20 nm to 300 nm, from 20 nm to 100 nm, or from 40 nm to 200 nm). As used herein, the maximum average dimension of a collection of particles is the sum of maximum dimension of the particles in the collection divided by the number of particles in the collection.

Structure

Within a population of metal carbonate (e.g., silver carbonate) particles, the individual particles can have a distribution of sizes, composition, and morphology. As an example, the metal carbonate particles can have a maximum average dimension of less than one micron (e.g., less than 750 nanometers, less than 500 nanometers, less than 250 nanometers, or less than 100 nanometers). In some embodiments, the metal carbonate particles have a maximum average dimension of around 50 nanometers (e.g., around 100 nanometers, around 250 nanometers, around 500 nanometers, or around 750 nanometers). The range of maximum average size of particles in a population can range from 20 nm to 500 nm (e.g., from 20 nm to 300 nm, from 20 nm to 100 nm, or from 40 nm to 200 nm). As used herein, the maximum average dimension is defined as the sum of maximum dimension of a number (n) of particles divided by (n).

Figure 1A:
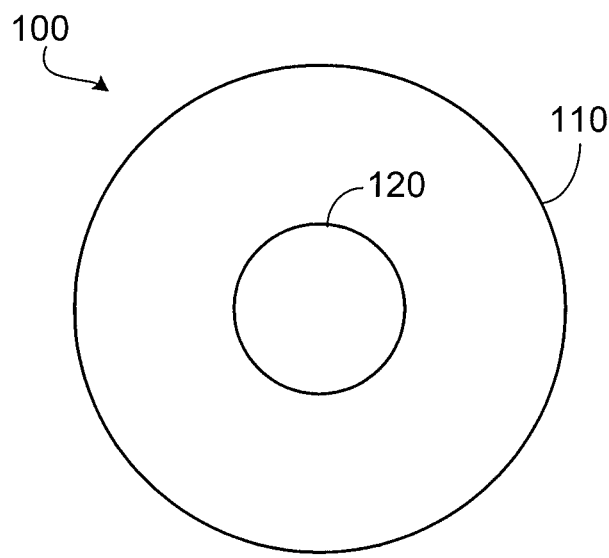
FIG. 1A is a cross-sectional view of an embodiment of a particle.

In some embodiments, the majority by weight of each metal carbonate particle is metal carbonate. For example, each particle can have more than 50% by weight (e.g., more than 60% by weight, more than 70% weight, more than 80% by weight, more than 90% by weight, or more than 95% by weight) or less than or equal to 100% by weight (less than 95% by weight, less than 90% by weight, less than 80% by weight, less than 70% by weight, less than 60% by weight) of metal carbonate. The metal carbonate can be uniformly dispersed throughout the particle, or be localized in a portion of the particle. For example, as shown in FIG. 1A, a particle 100 can include a metal carbonate shell 110 around a core 120 of a different material (e.g., silver, silver oxide). In some embodiments, the particle can include a metal carbonate core with a surrounding shell of a different material (e.g., silver, silver oxide).

In some embodiments, when the particles have a core-shell structure, the core can have an average maximum dimension of at most 200 nm (e.g., at most 150 nm, at most 100 nm, at most 50 nm, or at most 20 nm) and/or at least 2 nm (e.g., at least 20 nm, at least 50 nm, at least 100 nm, or at least 150 nm). The shell can have an average maximum thickness of at most 150 nm (e.g., at most 100 nm, at most 50 nm, or at most 20 nm) and/or at least 10 nm (e.g., at least 20 nm, at least 50 nm, or at least 100 nm). In some embodiments, the shell fully envelops the core structure. In some embodiments, the shell partially envelops the core structure. For example, the shell can cover at most 95% (e.g., at most 80%, or at most 75%) and/or at least 50% (e.g., at least 75%, at least 80%) of the core's surface area. The shell can have a uniform thickness or have variable thickness around the core. In some embodiments, a core-shell boundary is not clearly delineated. For example, the particles can have a graduated structure where a first component (e.g., silver carbonate) can increase (or decrease) in concentration relative to a second component (e.g., silver) from the core to the periphery of the particle.

The metal carbonate particles can be free of fatty acids (e.g., stearic acid, oleic acid). As an example, a population of metal carbonate particles can include 0% by weight of fatty acids (e.g., less than 0.01% by weight fatty acids, less than 0.02% by weight fatty acids, or less than 0.05% fatty acids). In some embodiments, the metal carbonate (e.g., silver carbonate) particles can be absent of metal oxide (e.g., silver oxide). For example, the particles can include 0% by weight of metal oxide (e.g., less than 0.5% by weight metal oxide, less than 1% by weight metal oxide, or less than 5% by weight metal oxide). The amount of metal oxide can be determined by powder X-ray diffraction, gravimetric analysis, and potentiometric titration. The amount of fatty acids can be determined by gravimetric analysis, gas chromatography, and/or infrared spectrometry.

In some embodiments, the metal carbonate particles can include an end-capping agent, such as polyvinyl alcohol. The end-capping agent can help control the size of the particles and/or stabilize the particles during formation, and decrease the likelihood of agglomeration.

The metal carbonate particles can be relatively spherical (e.g., have a sphericity of greater than 80%, greater than 90%, or greater than 95%). Sphericity is defined as the ratio of a surface area of a sphere with the same volume as a given particle to the surface area of the particle. In some embodiments, the particles are in the shape of a sphere. In some embodiments, the particles are polyhedrons having planar or curved surfaces. In some embodiments, the particles are irregularly shaped. Representative particles are shown, for example in FIGS. 6-9, described in more detail infra.

The particles can agglomerate to form clusters. In some embodiments, the clusters can have a maximum dimension of at most 25 microns (e.g., at most 20 microns, at most 15 microns, or at most 10 microns).

The metal carbonate in the particles can be nanocrystalline and/or atomically disordered. As referred to herein, an atomically disordered, crystalline material (e.g., an atomically disordered, nanocrystalline material) means a material that has more long range ordered, crystalline structure (a lesser degree of defects) than the material has in a fully amorphous state, but that also has less long range, ordered crystalline structure (a higher degree of defects) than the material has in a bulk crystalline state, such as in the form of a cast, wrought or plated material. Examples of defects include point defects, vacancies, line defects, grain boundaries, subgrain boundaries and amorphous regions. Point defects are defects on a size scale of no more than about four atomic spacings. A vacancy is the omission of an atom from its regular atomic site in the crystal lattice. Line defects are defective regions (e.g., edge dislocations, screw dislocations) that result in lattice distortions along a line (which may or may not be a straight line), and generally have a longer scale than point defects. In an edge dislocation, a lattice displacement is produced by a plane of atoms that forms a terminus of the lattice. In a screw dislocation, part of the lattice is displaced with respect to an adjacent part of the lattice. Grain boundaries separate regions having different crystallographic orientation or misorientation (e.g., high angle grain boundaries, low angle grain boundaries, including tilt boundaries and twist boundaries). Subgrain boundaries refer to low angle grain boundaries. An amorphous region is a region that does not exhibit long range, ordered crystalline structure. In certain embodiments, an atomically disordered, crystalline material (e.g., an atomically disordered, nanocrystalline material), when contacted with an alcohol or water-based electrolyte, is released into the alcohol or water-based electrolyte (e.g., as ions, atoms, molecules and/or clusters) over a time scale of at least about one hour (e.g., at least about two hours, at least about 10 hours, at least about a day). Examples of alcohols and/or water-based electrolytes include body fluids (e.g., blood, urine, saliva) and body tissue (e.g., skin, muscle, bone).

As referred to herein, a nanocrystalline metal carbonate is a single-phase polycrystal or a multi-phase polycrystal having a maximum dimension of about 100 nanometers or less (e.g., about 90 nanometers or less, about 80 nanometers or less, about 70 nanometers or less, about 60 nanometers or less, about 50 nanometers or less, about 40 nanometers or less, about 30 nanometers or less, about 25 nanometers or less) in at least one dimension.

Methods of Making the Particles

Figure 1B:
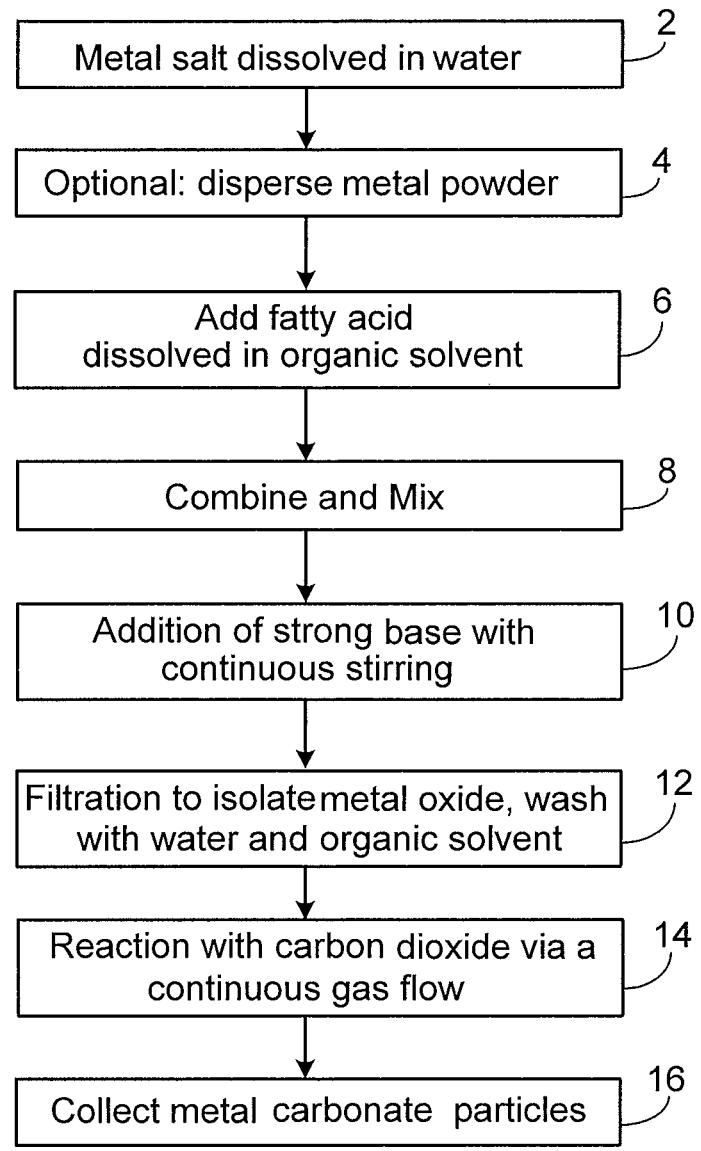
FIG. 1B is a flow chart illustrating an embodiment of a method of making a metal carbonate particle.

The metal carbonate particles can be made by a variety of methods. For example, referring to FIG. 1B, one method of making metal carbonate particles includes dissolving a quantity of a metal salt in water (e.g., deionized water) in a reaction vessel (Step 2). Optionally, a quantity of metal-containing powder (e.g., a silver powder) is dispersed into the metal salt solution to form a suspension (Step 4). A solution of fatty acid dissolved in a miscible organic solvent is then added to the metal salt and metal-containing powder suspension (Step 6), the mixture is stirred to mix (Step 8), and a solution of a base is slowly added to precipitate a metal oxide powder (Step 10). After filtration, the metal oxide powder is washed with water and one or more organic solvents (Step 12). The metal oxide powder is then exposed to a gaseous stream of $CO_2$ for an extended amount of time (Step 14) to afford metal carbonate particles (Step 16).

Figure 2:
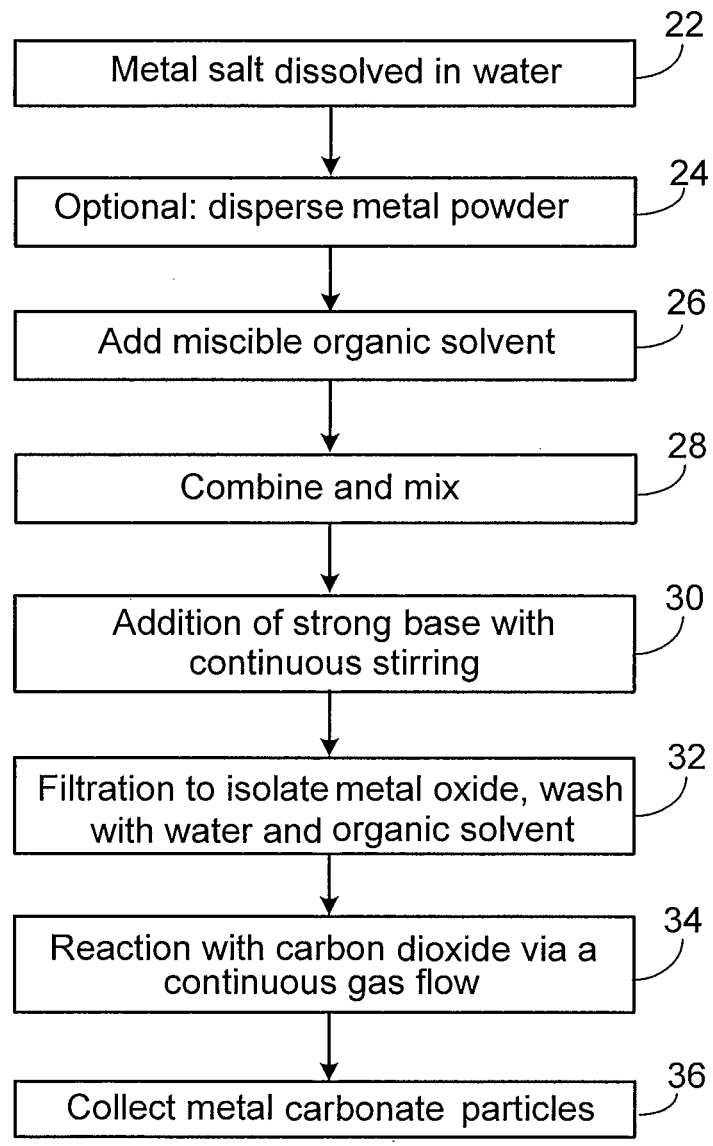
FIG. 2 is a flow chart illustrating an embodiment of a method of making a metal carbonate particle.

Referring to FIG. 2, another method of making metal carbonate particles includes dissolving a quantity of a metal salt in water (e.g., deionized water) in a reaction vessel (Step 22). Optionally, a quantity of metal-containing powder (e.g., a silver powder) is dispersed into the metal salt solution to form a suspension (Step 24). A quantity of a miscible organic solvent is then added to the metal salt solution (Step 26), the mixture is stirred to mix (Step 28), and a solution of a base is slowly added to precipitate a metal oxide powder (Step 30). After filtration, the metal oxide powder is washed with water and one or more organic solvents (Step 32). The metal oxide powder is then exposed to a gaseous stream of $CO_2$ for an extended amount of time (Step 34) to afford metal carbonate particles (Step 36).

Figure 3:
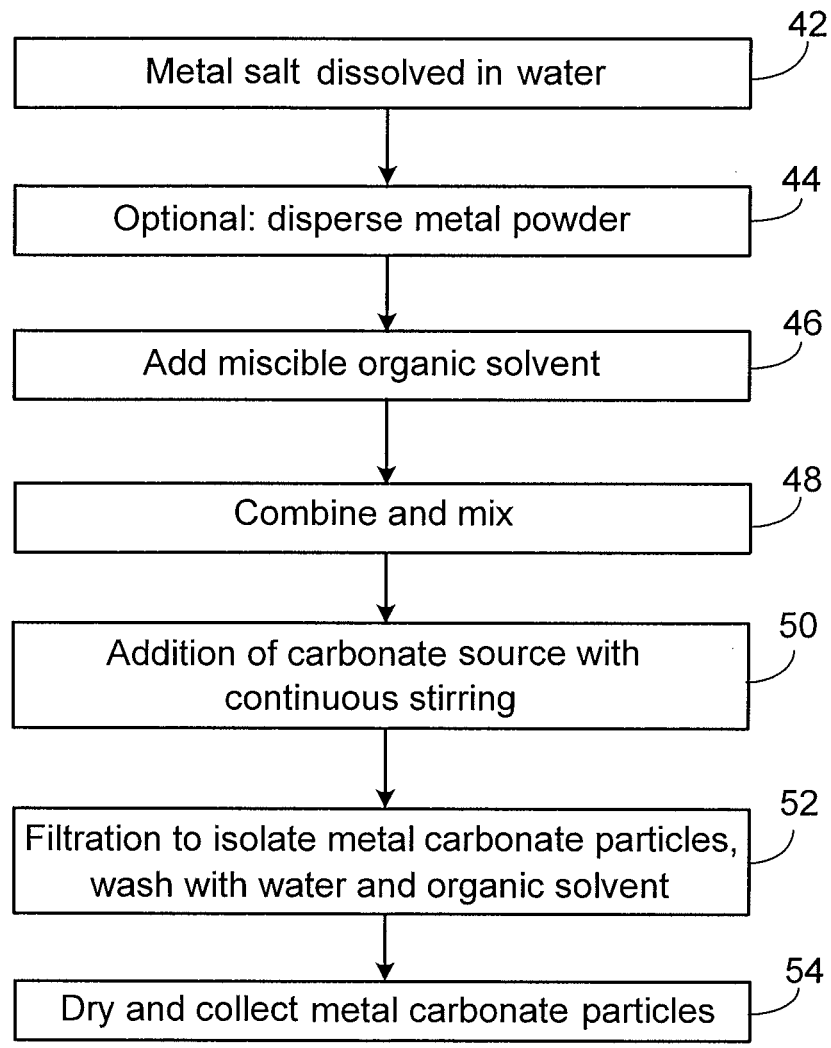
FIG. 3 is a flow chart illustrating an embodiment of a method of making a metal carbonate particle.

Referring to FIG. 3, yet another method of making metal carbonate particles includes dissolving a quantity of a metal salt in water (e.g., deionized water) in a reaction vessel (Step 42). Optionally, a quantity of metal-containing powder (e.g., a silver powder) is dispersed into the metal salt solution to form a suspension (Step 44). A quantity of a miscible organic solvent is then added to the metal salt solution (Step 46), the solution is mixed (Step 48), and a solution of a base containing a carbonate source is slowly added to directly form and precipitate metal carbonate particles (Step 50). After filtration, the metal carbonate particles are washed with water and one or more organic solvents (Step 52). The metal carbonate particles are then dried (e.g., in a stream of air for a period of less than 120 hours, less than 75 hours, less than 30 hours, or less than 18 hours) and collected (Step 54).

Figure 4:
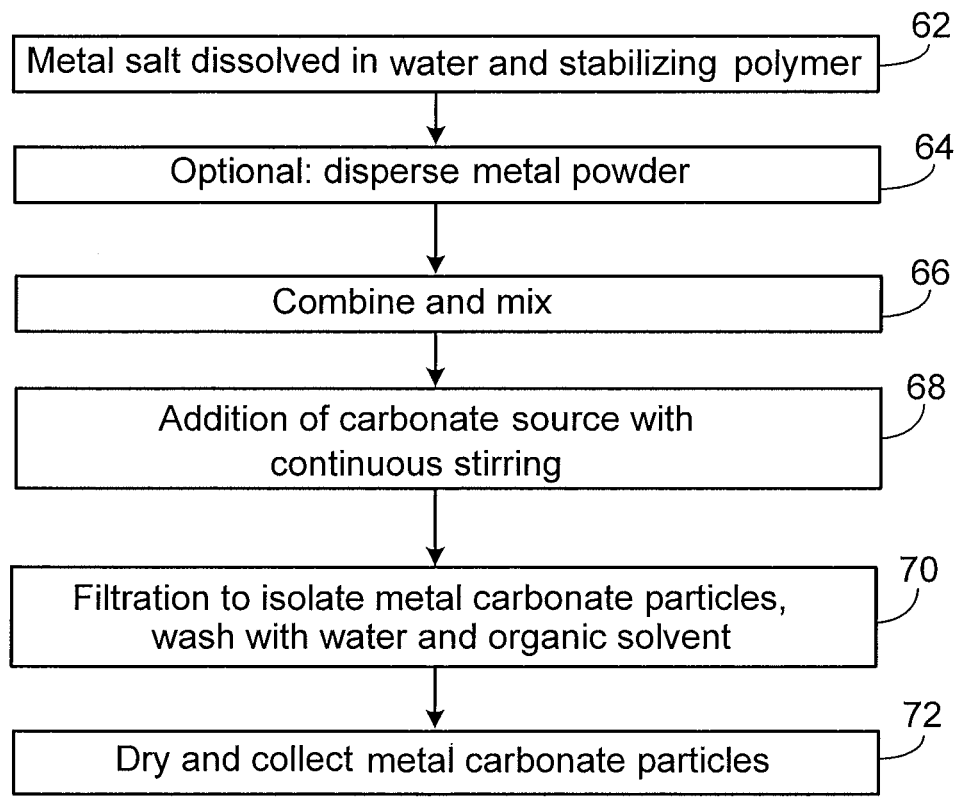
FIG. 4 is a flow chart illustrating an embodiment of a method of making a metal carbonate particle.

Referring to FIG. 4, yet another method of making metal carbonate particles include includes dissolving a quantity of a metal salt in water (e.g., deionized water) including a quantity of a stabilizing polymer, such as hydrolyzed polyvinyl alcohol, in a reaction vessel (Step 62). Optionally, a quantity of metal-containing powder (e.g., a silver powder) is dispersed into the metal salt solution to form a suspension (Step 64). The solution is mixed (Step 66), and a solution of a base containing a carbonate source (e.g., sodium carbonate) is slowly added to directly form and precipitate the metal carbonate particles (Step 68). After filtration, the metal carbonate particles are washed with water and/or one or more organic solvents (Step 70). The metal carbonate particles are then dried (in a stream of air for a period of less than 120 hours, less than 50 hours, less than 18 hours; or in a stream of air for a period of 18 to 120 hours) and collected (Step 72).

In some embodiments, examples of metal salts (e.g., silver salts) include metal nitrate, metal chlorate, metal fluoride, and metal perchlorate. In some embodiments, the metal salts include metal acetate and/or metal sulfate. In some embodiments, the metal salt is metal nitrate. The metal salt (e.g., silver nitrate) concentration in water can be between 2 and 5% by weight (e.g., between 2 and 4% by weight, or between 2 and 3 percent by weight). In some embodiments, the metal salt (e.g., silver nitrate) concentration in water is 2 percent by weight (e.g., 3 percent by weight, 4 percent by weight, or 5 percent by weight).

In some embodiments, the metal-containing powder (e.g., silver powder) that is optionally added to the metal salt solution has a maximum average dimension of at most 200 nm (e.g., at most 100 nm, at most 50 nm, at most 20 nm, at most 10 nm) and/or at least 2 nm (e.g., at least 5 nm, at least 10 nm, at least 20 nm, at least 50 nm, at least 100 nm). The metal-containing powder can serve as a nucleation site around which a metal carbonate shell can form.

In some embodiments, the fatty acids are optional. The fatty acids can include saturated and unsaturated fatty acids, such as stearic acid, myristic acid, palmitic acid, lauric acid, oleic acid, or linoleic acid. When a fatty acid is used in the reaction, the fatty acid concentration is less than 2% by weight (e.g., less than 1% by weight, less than 0.5% by weight, less than 0.2% by weight, less than 0.1% by weight, or less than 0.01% by weight) and/or more than 0.005% by weight (e.g., more than 0.01% by weight, more than 0.2% by weight, more than 0.5% by weight, or more than 1% by weight) of the dissolved metal in the metal salt solution. The fatty acid can help control the size of the particles and can decrease the likelihood of agglomeration. In some embodiments, washing the precipitated particles with one or more organic solvent (e.g., acetone, THF, methanol, ethanol) washes away any fatty acid molecules on the surface of the particles, such that the final particle product is free of fatty acids.

In some embodiments, the stabilizing polymer includes hydrolyzed polyvinyl alcohol and/or lecithin. When a stabilizing polymer is used in the reaction, the polymer concentration is less than 12% by weight (e.g., less than 10% by weight, less than 8% by weight, less than 5% by weight, less than 3% by weight, less than 1% by weight, less than 0.5% by weight, less than 0.2% by weight, less than 0.1% by weight, or less than 0.01% by weight) and/or more than 0.005% by weight (e.g., more than 0.01% by weight, more than 0.2% by weight, more than 0.5% by weight, or more than 1% by weight) of the dissolved metal in the metal salt solution. In some embodiments, the concentration of hydrolyzed polyvinyl alcohol is 0.1% by weight (e.g., 0.5% by weight). The stabilizing polymer can help control the size of the particles and can decrease the likelihood of agglomeration.

Examples of a base can include sodium hydroxide and/or potassium hydroxide. In some embodiments, the base includes a carbonate source for reaction with the metal salt (e.g., silver nitrate), such a base includes sodium carbonate, potassium carbonate, sodium bicarbonate, and/or potassium bicarbonate. The amount of base used in the reaction can be stoichiometric to the amount of metal salt present in the reaction vessel. In some embodiments the amount of base used in the reaction can be at a stoichiometric excess compared to the amount of metal salt present in the reaction vessel. The concentration of the base before addition to the metal salt mixture can be between two and ten weight percent (e.g., between two and eight weight percent, between two and six weight percent) in water. In some embodiments, the base concentration is between 4.5 weight percent and 6 weight percent.

In some embodiments, the miscible organic solvent is tetrahydrofuran, acetone, methanol, ethanol, dimethyl sulfoxide, dimethyl formamide, and/or 1-methylpyrrolidone. As used herein, miscible refers to an ability to be mixed. For example, two liquids are be miscible if they are partially or completely soluble in each other. The volume ratio of water to organic solvent in a metal salt mixture can range from 50:1 to 1:1 (e.g., from 20:1 to 1:1, from 10:1 to 1.1, or from 5:1 to 1:1). It is believed that the miscible organic solvent inhibits (e.g., decreases) growth of the metal carbonate crystals.

In some embodiments, the one or more organic solvents used to wash the particles after filtration is either miscible or immiscible with water. The one or more organic solvents can include, for example, acetone, tetrahydrofuran, methanol, ethanol, toluene, and 2-methyl tetrahydrofuran.

In some embodiments, the amount of time to which metal oxide is exposed to $CO_2$ gas extends from 18 hours to 120 hours. The amount of time varies depending on the concentration of $CO_2$. For example, metal oxide can be exposed to a gaseous stream 100% $CO_2$ for a shorter amount of time for conversion to metal carbonate.

It is believed that metal carbonate (e.g., silver carbonate) is more stable than metal oxide (e.g., silver oxide), so conversion of metal oxide to metal carbonate is favored. It is further believed that once metal carbonate particles form, the likelihood of agglomeration is unlikely to occur over time due to the stability of metal carbonate.

Characterization of Particles

The metal carbonate (e.g., silver carbonate) particles can be characterized in a variety of ways. For example, a sample of metal carbonate particles can be imaged by microscopy, such as scanning electron microscopy (SEM). The average dimensions of the particles within a population can be measured from a SEM image, for example, by adding the maximum dimensions of a representative number of particles and dividing the sum by the representative number of particles. The uniformity of coating and surface morphology of particles can also be determined from a SEM image.

In some embodiments, the metal carbonate particles are characterized by powder X-ray diffraction. A powder X-ray diffraction pattern can provide quantitative analysis of the amount of a metal material, such as metal carbonate or metal in the particles, for example, using Rietveld analysis. Signature peaks corresponding to a material can be obtained from, for example, the International Center for Diffraction Data database, and Norby et al., *Inorg. Chem.* 2002; 41(14); 3628-3637. As used herein, a peak has a signal to noise ratio of greater than 10:1.

In some embodiments, the total metal (e.g., silver) content of a sample of metal carbonate (e.g., silver carbonate) particles can be determined by gravimetric analysis. For example, in gravimetric analysis, a silver carbonate particle sample is dissolved in nitric acid and silver is precipitated from the solution as silver chloride following addition of sodium chloride. The precipitate is then filtered, dried, and weighed. Stoichiometric relationships are then used to deduce the amount of silver present in the precipitate from the sample.

In some embodiments, for a metal carbonate particle such as silver carbonate particle, the percentage of silver carbonate in the particles can then be determined via potentiometric acid-base titrations. Here, the particles are sonicated with an aqueous solution of sodium chloride (NaCl), solid silver carbonate ($Ag_2CO_3(s)$) is quantitatively converted to solid silver chloride (AgCl(s)), releasing into solution sodium carbonate ($Na_2CO_3$):

$$Ag_2CO_3(s) + 2Cl^- \rightarrow 2AgCl(s) + CO_3^{2-}$$

The extract solution, which contains $CO_3^{2-}$, is titrated with hydrochloric acid solution using a pH-meter to potentiometrically follow solution pH versus amount of added titrant. The volume of HCl titrant consumed at the first equivalence point corresponds to the conversion of carbonate to bicarbonate:

$$CO_3^{2-} + HCl \rightarrow HCO_3^- + Cl^-$$

The volume of HCl titrant required to go from the first to the second equivalence point ($\Delta V_{HCl}$) corresponds to the conversion of bicarbonate to the carbonic acid (or to carbon dioxide and water):

$$HCO_3^- + HCl \rightarrow H_2CO_3 + Cl^- \rightarrow CO_2 + H_2O$$

By calculating the amount of HCl needed to titrate the particles, the amount of silver carbonate in the particles can be determined.

Formulations

The metal carbonate particles can be a component of a formulation such as a cream, a nanodispersion, a solution, a powder (e.g., a freeze-dried powder), a foam, a gel, a lotion, a paste, an ointment, a spray, a drop, or a suppository, each having a specific formulation. In general, depending on the formulation, the metal carbonate particles can be used to treat a variety of conditions. For example, a therapeutically effective amount of a cream, nanodispersion, solution, foam, gel, lotion, paste, ointment, spray, or drop, or powder including the metal carbonate particles can be used to treat skin conditions by directly administering to the affected areas in a subject. Treatment can continue until the condition ameliorates or disappears.

In some embodiments, various formulations can optionally include one or more components which can be biologically active or biologically inactive. Examples of such optional components include base components (e.g., water and/or an oil, such as liquid paraffin, vegetable oil, peanut oil, castor oil, cocoa butter), thickening agents (aluminum stearate, hydrogenated lanolin), gelling agents, dispersing agents, suspending agents, thickening agents, coloring agents, perfumes, excipients (starch, tragacanth, cellulose derivatives, silicones, bentonites, silicic acid, talc), foaming agents (e.g., surfactants), surface active agents, preservatives (e.g., methyl paraben, propyl paraben, benzyl alcohol), and cytoconductive agents (e.g., betaglucan). In certain embodiments, a pharmaceutical carrier composition can include a constituent (e.g., DMSO) to assist in the penetration of skin. In some embodiments, a formulation can include tinting agents, emollients, skin conditioning agents, humectants, preservatives, antioxidants, perfumes, chelating agents: physically and chemically compatible with other components of the composition.

Formulations are described, for example, in U.S. application Ser. No. 11/766,897, filed Jun. 22, 2007, herein incorporated by reference in its entirety.

Conditions

In some embodiments, depending on the condition to be treated, a cream, lotion, gel, solution, nanodispersion, and/or ointment containing the metal carbonate particles can be topically applied, for example, to an area of the skin to improve an infection, for example, a microbial wound infection. In some embodiments, the metal carbonate are applied to a dressing or a medical device, and applied to an area (e.g., a wounded area) of a subject.

In some embodiments, depending on the condition to be treated, a solution and/or a nanodispersion containing the metal carbonate particles can contact an area having mucous membranes such as mouth, eyes, colon, lungs, and/or other organs, in the form of a rinse, a bath, a wash, an enema, a gargle, a spray, and/or drops, with or without the use of a device. As an example, the solution and/or the nanodispersion can be injected into a subject using a small needle injector and/or a needleless injector. As an another example, the solution and/or the nanodispersion containing the metal carbonate particles can be formed into an aerosol (e.g., an aerosol prepared by a mechanical mister, such as a spray bottle or a nebulizer), and the aerosol can be contacted with the subject using an appropriate device (e.g., a hand held inhaler, a mechanical mister, a spray bottle, a nebulizer, an oxygen tent). As a further example, a solution and/or nanodispersion containing the metal carbonate particles can be contacted with the subject via a catheter.

In some embodiments, the metal carbonate particles is in the form of an aerosol or dry powder, formed from lyophilizing, freeze-drying, or drying a nanodispersion. The aerosol or dry powder can be inhaled to contact a respiratory area such as the mouth, lungs, or nasal passage for treatment of respiratory conditions. In some embodiments, the metal carbonate particles in the form of an article such as a suppository, solution, nanodispersion, tablet, capsule, pill, or foam can contact the gastrointestinal system of a subject to treat, for example, inflammatory bowel disease (IBD), biofilm conditions, or C. dfficile infections. The article can include a sustained release formulation (e.g., a sustained release capsule) which can allow the metal carbonate particles to be released at a predetermined rate (e.g., a relatively constant rate). In some embodiments, an article can include a metal carbonate particles (e.g., in the form of a coating and/or in the form of a matrix material) that allows the article to pass through certain portions of the gastrointestinal system with relatively little (e.g., no) release of the metal carbonate particles, but that allows a relatively large amount of the metal carbonate particles to be released in a desired portion of the gastrointestinal system. As an example, the article can be an enteric article (e.g., an enteric coated tablet, an enteric coated capsule, an enteric coated pill) so that the formulation passes through the stomach with little (e.g., no) metal carbonate particles being released, and so that the metal carbonate particles are relatively easily released by the article in the intestines. In some embodiments, the article can be an enema or a suppository, which can contact the gastrointestinal system (e.g., the colon) to provide a therapeutic effect.

The metal carbonate particles can be used to treat one or more conditions. In some embodiments, the conditions that are treated with the metal carbonate particles are mucosal or serosal conditions, skin conditions, respiratory conditions, musculo-skeletal conditions, and/or circulatory conditions. The conditions can be caused by bacteria, inflammation, hyperproliferation, fungi, viruses, protozoa, autoimmune responses, or toxic or damaging substances produced by bacteria, virus, fungi, or protozoa. In some embodiments, the conditions can include wounds (e.g., burns, cuts, or open wounds). In some embodiments, the conditions are idiopathic in nature.

The conditions could be the same type of condition (e.g., multiple skin or integament conditions) or different types of conditions. For example, a cream containing metal carbonate particles can be applied to an area of the skin having multiple skin or integument conditions (e.g., a burn and psoriasis) so that the metal carbonate particles treat the multiple skin or integument conditions.

Moreover, while the foregoing has described embodiments that involve one method of contacting a subject with the metal carbonate particles, in other embodiments, more than one method of contacting a subject with the metal carbonate-containing particles can be used.

Furthermore, while the foregoing has described embodiments in which one form of the metal carbonate particles is used, in other embodiments, more than one form of the metal carbonate particles can be used. For example, the methods can include using the metal carbonate particles in the form of a cream, a freeze-dried powder, a solution, and/or a nanodispersion.

Examples of conditions and treatment methods are described, for example, in U.S. application Ser. No. 11/766, 897, filed Jun. 22, 2007, herein incorporated by reference in its entirety.

EXAMPLES

Example 1

Preparation of Silver Carbonate Particles Including a Nanocrystalline Silver Carbonate on a Silver Core (Silver Carbonate/Silver Core Shell Structure)

A 10 gram batch of particles was produced following the procedure described below:

Approximately 7.87 grams of ACS grade silver nitrate (Sigma-Aldrich) was dissolved by stirring at room temperature in 125 mL of high-purity water (18.2 MΩ cm) in a 250 mL Pyrex reaction vessel. Five grams of silver powder (Sigma-Aldrich) were added to the silver nitrate solution to form nucleation sites and the mixture was dispersed by rapid stirring. While stirring, a second solution consisting of 109 mg stearic acid dissolved in 25 mL acetone was added; creating a cloudy emulsion. To this emulsion 33.3 mL of a 5.3% sodium hydroxide solution was slowly added (~1 mL/min), thus forming a dark gray/brown precipitate. The precipitate and solution was transferred to a Buchner funnel filtration set-up containing a Whatman filter paper and rinsed thoroughly with deionized water (5-7 times) followed by a final rinse using 25 mL of acetone. The powder remained on the filter paper with the vacuum pump running for approximately 68 hours.

Figure 5:
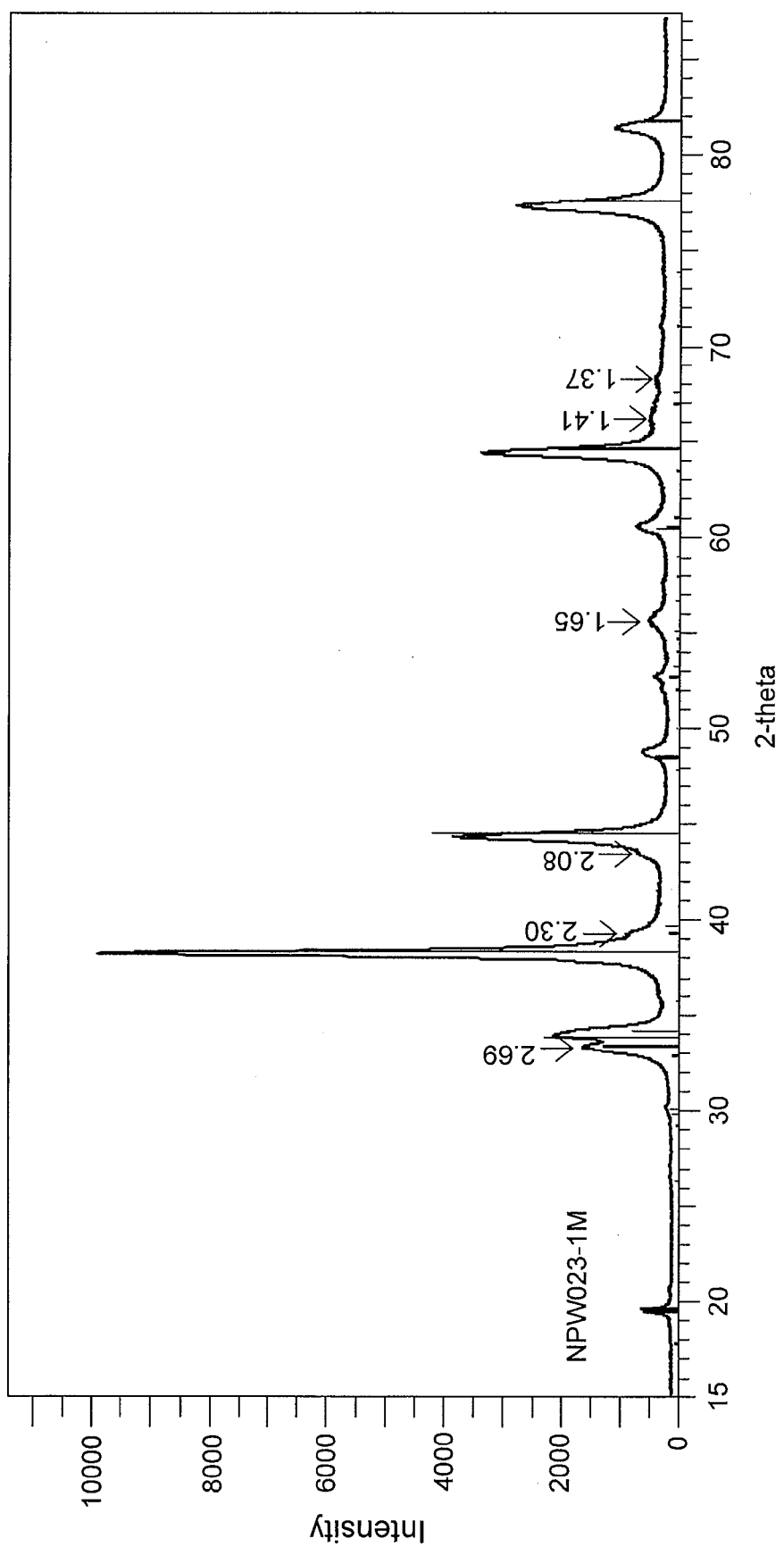
FIG. 5 is a X-ray diffraction pattern of an embodiment of silver carbonate particles.
Figure 6:
FIG. 6 is a microscopic view of an embodiment of silver carbonate particles.

Referring to FIG. 5, higher temperature silver carbonate polymorphs were confirmed by x-ray analysis. Referring to FIG. 6, the silver carbonate particles are agglomerated and have an average dimension of about 100 nanometers.

Analysis of total silver via gravimetric precipitation resulted in a total silver wt % of 92.21% supporting the x-ray results of only $Ag^0$ and silver carbonate present.

Example 2

Preparation of Silver Carbonate Particles Using a Mixed Solvent System

Five gram batches of powder were produced following the procedure described below.

Approximately 7.87 grams of ACS grade silver nitrate (Sigma-Aldrich) was dissolved by stirring at room temperature in 125 mL of high-purity water (18.2 MΩcm) in a 250 mL glass reaction vessel. After approximately 2 minutes, once the silver nitrate was completely dissolved, 25 mL of a water miscible solvent (tetrahydrofuran (THF), acetone, or methanol) was added with rapid stirring. This solution was stirred for not less than 1 minute to ensure adequate phase mixing. To this solution, 33.3 mL of approximately 5.3% sodium hydroxide was added at a rate of approximately 1 mL/min with stirring. A dark gray brown precipitate was observed. This product was collected via vacuum filtration using a standard Buchner setup and rinsed thoroughly with deionized water (5-7 times) before allowing an atmospheric air composition to flow over the material until dry.

Figure 7:
FIG. 7 is a microscopic view of an embodiment of silver carbonate particles.
Figure 8:
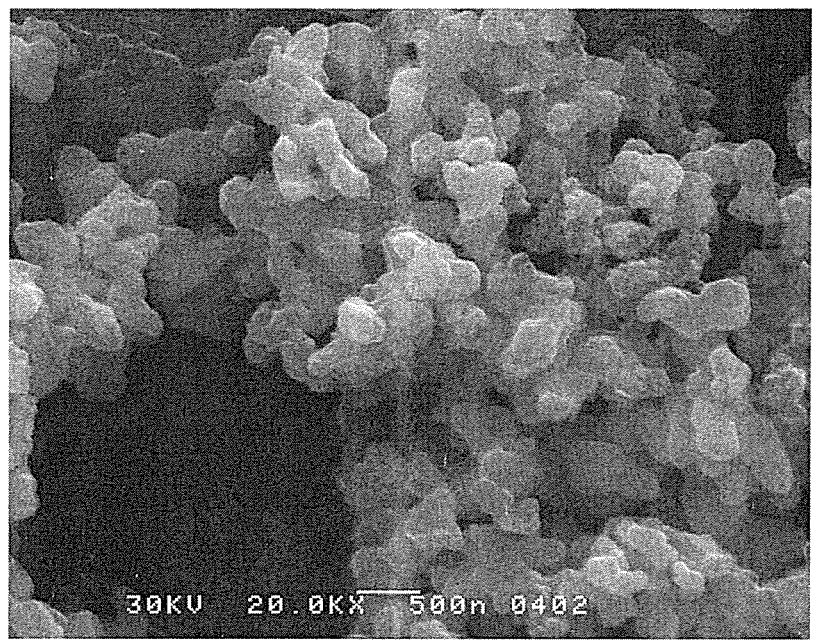
FIG. 8 is a microscopic view of an embodiment of silver carbonate particles.
Figure 9:
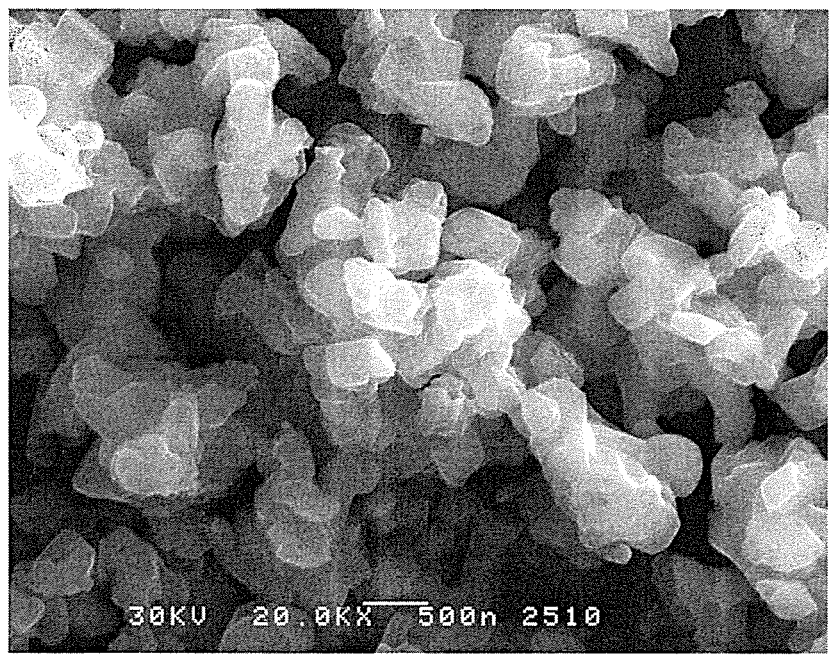
FIG. 9 is a microscopic view of an embodiment of silver carbonate particles.

Total silver analysis via gravimetric precipitation confirmed high silver carbonate levels for each of the three batches. Total silver results were 80.43, 79.99, and 81.97 wt % for the THF, acetone, and methanol batches respectively. Potentiometric titration of the water/THF batch resulted in an assay of 88% silver carbonate. A representative SEM image of particles produced from a mixture of water and THF is shown in FIG. 7. A representative SEM image of particles produced from a mixture of water and acetone is shown in FIG. 8. A representative image of particles produced form a mixture of water and methanol is shown in FIG. 9.

Example 3

Preparation of Silver Carbonate Particles Using a Mixed Solvent system

A 5 gram batch of powder was produced following the procedure described below:

Approximately 7.87 grams of ACS grade silver nitrate (Sigma-Aldrich) was dissolved by stirring at room temperature in 125 mL of high-purity water (18.2 MΩcm) in a 250 mL glass reaction vessel. Once the silver nitrate was completely dissolved 25 mL of a water miscible solvent (THF) was added with rapid stirring. This solution was stirred for not less than 1 minute to ensure adequate phase mixing. To this solution, 50 mL of approximately 10% sodium carbonate was added at a rate of approximately 1 mL/min with stirring. A yellow precipitate was observed. The precipitate and solution was transferred to a Buchner funnel filtration set-up containing a Whatman filter paper and rinsed thoroughly with deionized water (5-7 times) followed by a final rinse using 25 mL of THF. The powder remained on the filter paper with the vacuum pump running for approximately 22 hrs. The final powder appeared tan in color.

Total silver analysis via gravimetric precipitation resulted in a total silver wt % of 76.44%, thus confirming high silver carbonate levels for this batch.

Example 4

Preparation of Silver Carbonate Particles in and Aqueous Solution, Using hydrolyzed PVA Two 5 gram batches of powder were produced following the procedure described below:

Approximately 7.87 grams of ACS grade silver nitrate (Sigma-Aldrich) was dissolved by stirring at room temperature in 125 mL of hydrolyzed PVA (0.1% or 0.5%) in a 250 mL glass reaction vessel. To this solution, 50 mL of approximately 10% sodium carbonate was added at a rate of approximately 1 mL/min with stirring. A white precipitate was observed. The precipitated product was collected via vacuum filtration using a standard Buchner setup and rinsed thoroughly with deionized water (5-7 times) before allowing an atmospheric air composition to flow over the material until dry. The final powder appeared tan in color.

Total silver analysis via gravimetric precipitation resulted in 77.29 and 77.34 wt % silver for the 0.1% and 0.5% batches respectively, thus confirming high silver carbonate levels for these batches.

Example 5

Preparation of Silver Carbonate Including Addition of Oleic Acid

Reagent Preparation

Silver Nitrate Solution: using a graduated cylinder, 125 mL of high-purity water was transferred to a 250 mL glass titration vessel. 7.87009 g of silver nitrate was weighed out using a balance, quantitatively transferred to the 250 mL glass titration vessel, and stirred until completely dissolved.

Oleic Acid Solution: 58.18 mg of oleic acid was added to a 25 mL volumetric flask. ~15 mL of acetone was added to the flask and the solution was mixed until the oleic acid was completely dissolved. Acetone was then added to bring the final volume to 25 mL.

Sodium Hydroxide Solution: 47.8 g of 50.6% sodium hydroxide was weighed into a 1 L amber bottle. High-purity water was then added to the bottle bringing the total mass to 446.4 g. Solution was then stirred until completely dissolved.

% NaOH=(47.8 g*50.6%)/446.4 g=5.4% w/w

Procedure

The silver nitrate solution was prepared and attached to a titrator. Using the stir function in the LabX light software, the solution was mixed at a speed of 50%. While the silver nitrate was mixing, the oleic acid solution was slowly added to the titration vessel (creating a white/cloudy emulsion in the vessel). While the silver nitrate and oleic acid solutions were well mixing the sodium hydroxide solution was added to the mixture dropwise to dispense at the rate of 0.6 mL/min until an excess of hydroxide ions had been added; precipitating all the silver ions present.

Following the completion of the precipitation step the material was quantitatively transferred to a buchner funnel set up containing a Whatman #3 filtration paper. A gray black powder (with some white flakes) was collected on the filter paper and rinsed multiple times (5-7) with high-purity water. A final rinse was then performed using ~25 mL of acetone. This rinse redissolved the white flakes (oleic acid) that had been visible and helped accelerate the drying process. The Buchner funnel was loosely covered with a paper towel and allowed to pull a vacuum over the weekend to ensure the collected powder was completely dry.

Following the drying step, the powder was collected and ground with a mortar and pestle to break up the large chunks that had formed. The fine powder was then transferred to a 20 mL amber vial and overlaid with argon for storage until characterization testing could be performed.

Following the procedure described above a fine brown/gray powder was prepared with a % yield of 89%.

Example 6

Preparation of Silver Carbonate Particle Including Addition of Stearic Acid

Reagent Preparation

Silver Nitrate Solution: using a graduated cylinder, 125 mL of high-purity water was transferred to a 250 mL glass titration vessel. 7.86770 g of silver nitrate was weighed out using a balance, quantitatively transferred to the 250 mL glass titration vessel, and stirred until completely dissolved.

Stearic Acid Solution: 54.34 mg of stearic acid was added to a 25 mL volumetric flask containing approximately 15 mL of acetone. The solution was mixed until the stearic acid was completely dissolved and acetone was then added to bring the final volume to 25 mL.

Sodium hydroxide solution: 46.8 g of 50.6% sodium hydroxide was weighed into a 1 L amber bottle. High-purity water was then added to the bottle bringing the total mass to 446.6 g. Solution was then stirred until completely dissolved. % NaOH=(46.8 g*50.6%)/446.6 g=5.3% w/w.

Procedure

The silver nitrate solution was prepared and attached to the titrator. Using the stir function in the LabX light software, the solution was mixed at a speed of 50%. While the silver nitrate was mixing, the stearic acid solution was slowly added to the titration vessel (creating a white/cloudy emulsion in the vessel). While the silver nitrate and stearic acid solutions were well mixing the sodium hydroxide solution was added to the mixture dropwise using the titrator to dispense at the rate of 0.6 mL/min until an excess of hydroxide ions had been added; precipitating all the silver ions present.

Following the completion of the precipitation step the material was quantitatively transferred to a buchner funnel set up containing a Whatman #3 filtration paper. A gray black powder (with some white flakes) was collected on the filter paper and rinsed multiple times (5-7) with high-purity water. A final rinse was then performed using ~25 mL of acetone. This rinse redissolved the white flakes (stearic acid) that had been visible and helped accelerate the drying process. The buchner funnel was loosely covered with a paper towel and allowed to pull a vaccuum over the weekend to ensure the collected powder was completely dry.

Following the drying step, the powder was collected and ground with a mortar and pestle to break up the large chunks that had formed. The fine powder was then transferred to a 20 mL amber vial and overlaid with argon for storage until characterization testing could be performed.

% Yield was 100.6%, which could be due to insufficient drying, or incomplete removal of sodium nitrate during the water rinse steps.

Example 7

Zone of Inhibition Assay and Minimum Inhibitory Concentration

Standard Well Zone of Inhibition assay and Broth Microdilution MIC assay were both carried out using *Pseudomonas aeruginosa* Type strain ATCC 9027, *Staphylococcus aureus* Type strain ATCC 6538, *Escherichia coli* Type strain ATCC 8739, *Candida albicans* Type strain ATCC 10231, and *Aspergillus fumigatus* Type strain ATCC 90906. Modified Kirby-Bauer Zone of Inhibition Assay Organisms cultured on Mueller-Hinton Agar ("MHA", for bacteria) or Sabouraud Dextrose Agar ("SDA" for fungi) were harvested with a sterile disposable inoculating loop, were resuspended in Mueller-Hinton Broth ("MHB", for bacteria) or Sabouraud Dextrose Broth ("SDB", for fungi) to an optical density equivalent to a McFarland 0.5 standard, and the suspension was streaked onto fresh MHA or SDA. The MHA or SDA plates were then allowed 5 minutes for the inoculum to dry, then 6-mm diameter wells were cut into the agar with a sterile cork bore to accommodate the silver preparations (Note: this differs from a standard Kirby-Bauer Assay where antimicrobials are added in the form of antimicrobial-impregnated paper disks). A 100 µl-portion of each preparation was then placed into each well. The plates were incubated overnight at 37° C. right-side up (note: this differs from a standard Kirby-Bauer Assay where the plates are incubated inverted). The circular inhibition zones were measured at their diameters.

Bacterial Minimal Inhibitory Concentration Assay

Bacteria cultured on MHA were harvested with a sterile disposable inoculating loop, and were resuspended in Mueller-Hinton Broth to an optical density equivalent to a McFarland 0.5 standard. This suspension was then diluted 1:5 in fresh MHB, and the dilution incubated at 37° C. until its turbidity was again equivalent to that of a McFarland 0.5 standard. The culture was diluted 1:30 in fresh MHB, and the 1:30 dilution used as the inoculum for the assay.

Stock solutions of silver preparations were added to wells in a 96-well microtiter plate, and were serially diluted by transferring 100 µl of each well into another well containing 100 µl fresh MHB. Each serial dilution was then inoculated with 10 µl of the 1:30-diluted bacterial suspension. Plates were incubated 16-24 hours at 37° C. and growth was assessed by measuring the optical density of the cultures at 620 nm. Each assay was performed in quadruplicate, and the MIC was taken as the concentration of silver at which none of the four quadruplicate tests demonstrated growth.

Fungal Minimal Inhibitory Concentration Assay

Fungi cultured on Sabouraud Dextrose Agar (SDA) were harvested with a sterile disposable inoculating loop, and were resuspended in Sabouraud Dextrose Broth to an optical density equivalent to a McFarland 0.5 standard. This suspension was then diluted 1:1000 in fresh SDB, and the dilution used as the inoculum for the assay.

Stock solutions of silver preparations were added to wells in a 96-well microtiter plate, and were serially diluted by transferring 100 µl of each well into another well containing 100 µl fresh SDB. Each serial dilution was then inoculated with 100 µl of the 1:1000-diluted fungal suspension. Plates were incubated 48-72 hours at 23° C. and growth was assessed by measuring the optical density of the cultures at 620 nm. Each assay was performed in quadruplicate, and the MIC was taken as the concentration of silver at which none of the four quadruplicate tests demonstrated growth.

Results and Discussion:

All formulations except negative control had in vitro antimicrobial activity against all test strains (Tables 1 and 2). The MICs measured for *Candida albicans* (15-17 ppm) are somewhat higher than MICs typically measured for this strain (typically 1-2 ppm) for silver. However, the other fungus tested (Aspergillusfumigatus) were inhibited by the preparations with MICs typical of silver.

TABLE 1

MIC (in ppm) of silver carbonate preparations versus three bacterial test strains and two fungal test strains.

| Sample | | Silver content (w/v %) | E coli | P aerug | S aureus | C albic | A fumig |
|---|---|---|---|---|---|---|---|
| 1 | Placebo (negative control) | None | n.i. | n.i. | n.i. | n.i. | n.i. |
| 2 | $Ag_2CO_3$ homogenized in 0.5% $PVA_{(aq)}$ | 0.387% | 8 | 4 | 8 | 15 | 1 |
| 3 | $Ag_2CO_3$ homogenized in 0.5% $PVA_{(aq)}$ | 0.424% | 17 | 4 | 8 | 17 | 2 |
| 4 | $Ag_2CO_3$ homogenized in 0.5% $PVA_{(aq)}$ | 0.430% | 4 | 4 | 8 | 17 | 2 |
| 5 | $Ag_2CO_3$ homogenized in 0.5% $PVA_{(aq)}$ | 0.436% | 4 | 4 | 9 | 17 | 1 | n.i. = no inhibition was observed at any tested dilution.

TABLE 2

Inhibition zone diameters (in mm)) of silver carbonate preparations versus three bacterial test strains and two fungal test strains. All zone measurements include the 6-mm diameter of the well.

| Sample | | Silver content (w/v %) | E coli | P aerug | S aureus | C albic | A fumig |
|---|---|---|---|---|---|---|---|
| 1 | Placebo (negative control) | None | none | none | none | none | none |
| 2 | $Ag_2CO_3$ homogenized in 0.5% $PVA_{(aq)}$ | 0.387% | 8 | 12 | 13 | 14 | 17 |
| 3 | $Ag_2CO_3$ homogenized in 0.5% $PVA_{(aq)}$ | 0.424% | 8 | 11 | 12 | 14 | 17 |
| 4 | $Ag_2CO_3$ homogenized in 0.5% $PVA_{(aq)}$ | 0.430% | 8 | 12 | 13 | 14 | 17 |
| 5 | 0.5% $Ag_2CO_3$ homogenized in 0.5% $PVA_{(aq)}$ | 0.436% | 8 | 11 | 12 | 14 | 18 | none = no inhibition zone was observed.

Example 8

In Vivo Barrier to Infection Mouse Model

An emollient cream containing 1% silver carbonate particles was compared to a nanocrystalline silver cream and a placebo cream in an in vivo mouse model designed to measure barrier-to-infection efficacy. In this experiment (FIG. 10), both the silver carbonate particle cream and the nanocrystalline silver cream reduced recoverable CFU of MRSA by 1.5-2.0 logs relative to placebo cream, which was significant ($p<0.05$ by Kriskal-Wallis ANOVA on Ranks).

Mice were anesthetized with I.P. ketamine/xylazine, and a wound was produced on a small area (approx 1 cm×1 cm) by repeatedly stripping with Elastocon bandaging. The wound sites were then coated with 1% nanocrystalline silver cream, 1% silver carbonate particle containing cream, or placebo cream, or were left uncoated. Creams were applied to a thickness at which the wound was not visible. A sterile paper disk approx 5 mm diameter was then applied to the wound/cream, and five microliters of prepared bacterial suspension (stationary-phase overnight cultures suspended in 0.1% peptone water to approximately $10^8$ cfu/ml) was applied to the disk. Mice were housed individually. Three days after the procedure, mice were sacrificed and bacterial burden at the wound site was determined by swabbing.

Figure 10:
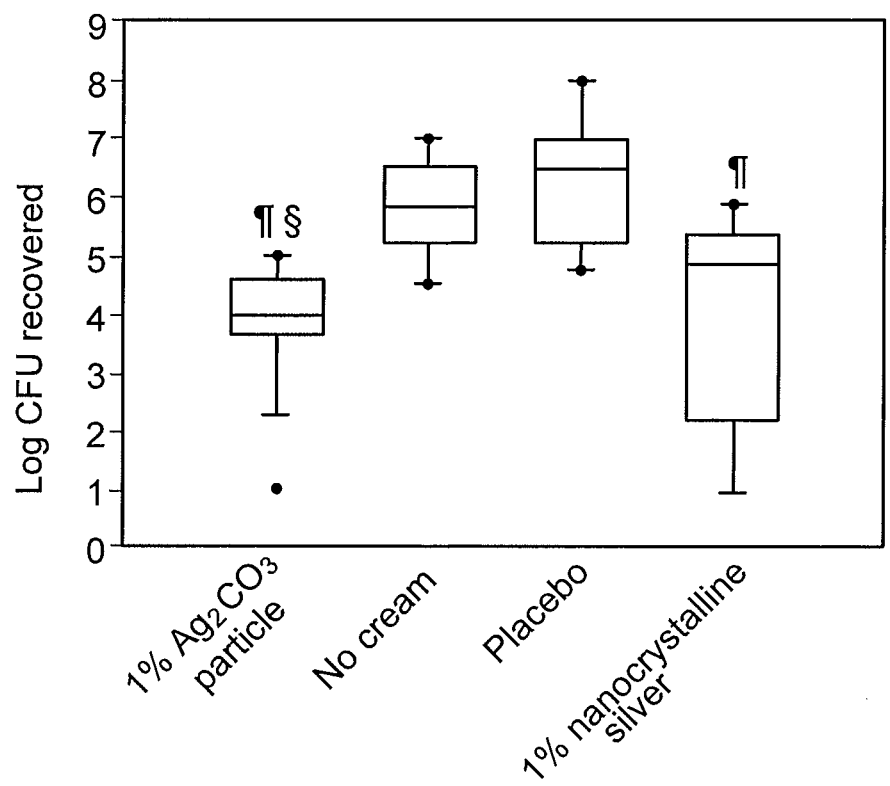
FIG. 10 is a chart showing the barrier-to-infection properties of emollient creams including 1% nanocrystalline silver or silver carbonate particles.

As shown in FIG. 10, creams containing the silver carbonate particles served as a barrier to infection, whereas placebo cream did not. Each box in FIG. 10 indicates limits of upper and lower quartiles; line through box indicates median; bars above and below box indicate 90th and 10th percentiles, respectively; individual outliers are indicated by dots. ¶=Significantly different than Placebo Cream. §=Significantly different than No Cream.

These preliminary data suggest that the silver carbonate particles have antimicrobial activity that is comparable to that of nanocrystalline silver, both in in vitro MIC and zone-of-inhibition assays, and in an in vivo barrier-to-infection mouse model.

A number of embodiments of the invention have been described, but other embodiments are possible. As an example, metals other than silver (e.g., platinum, palladium, gold, titanium, cobalt, nickel, rhodium, ruthenium, iron, copper, zinc, mercury, cadmium) may be used in the methods and/or particles. In some embodiments, in a core-shell structure, a core includes one or more different metals, metal oxides, and/or metal carbonates than an outer shell including one or more metals, metal oxides, and/or metal carbonates. Nevertheless, it will be understood that various modifications may be made without departing from the spirit and scope of the invention.

All references, such as patent applications, publications, and patents, referred to herein are incorporated by reference in their entirety.

Other embodiments are in the claims.

What is claimed is:

1. A particle, consisting of:
   a metal carbonate; and
   a metal;
   wherein the particle contains more than 70 percent by weight of the metal carbonate, and the particle has an average maximum dimension of less than 500 nanometers.

2. The particle of claim 1, wherein the particle consists of a metal carbonate outer shell around a metal core.

3. The particle of claim 1, wherein the metal carbonate is uniformly dispersed throughout the particle.

4. The particle of claim 1, wherein the metal is silver.

5. The particle of claim 1, wherein the metal carbonate is silver carbonate.

6. A pharmaceutical composition, comprising:
   a particle comprising a metal carbonate and a metal; and
   a pharmaceutically acceptable carrier,
   wherein the particle contains more than 70 percent by weight of the metal carbonate, and the particle has an average maximum dimension of less than 500 nanometers.

7. The composition of claim 6, wherein the metal carbonate is uniformly dispersed throughout the particle.

8. The composition of claim 6, wherein the composition is a cream, a nanodispersion, a solution, a foam, a gel, a lotion, a paste, an ointment, a spray, a drop, or a suppository.

9. A pharmaceutical composition, comprising:
   a particle consisting of a metal carbonate outer shell around a metal core; and
   a pharmaceutically acceptable carrier,
   wherein the particle contains more than 70 percent by weight of the metal carbonate, and the particle has an average maximum dimension of less than 500 nanometers.

10. The composition of claim 9, wherein the metal is silver.

11. The composition of claim 9, wherein the metal carbonate is silver carbonate.

12. The composition of claim 9, wherein the composition is a cream, a nanodispersion, a solution, a foam, a gel, a lotion, a paste, an ointment, a spray, a drop, or a suppository.

13. A pharmaceutical composition, comprising:
    a particle comprising a metal carbonate and a metal, the metal being silver; and
    a pharmaceutically acceptable carrier,
    wherein the particle contains more than 70 percent by weight of the metal carbonate, and the particle has an average maximum dimension of less than 500 nanometers.

14. The composition of claim 13, wherein the particle consists of a metal carbonate outer shell around a metal core.

15. The composition of claim 13, wherein the metal carbonate is uniformly dispersed throughout the particle.

16. The composition of claim 13, wherein the metal carbonate is silver carbonate.

17. The composition of claim 13, wherein the composition is a cream, a nanodispersion, a solution, a foam, a gel, a lotion, a paste, an ointment, a spray, a drop, or a suppository.

18. A pharmaceutical composition, comprising:
    a particle comprising a metal carbonate and a metal, the metal carbonate being silver carbonate; and
    a pharmaceutically acceptable carrier,
    wherein the particle contains more than 70 percent by weight of the metal carbonate, and the particle has an average maximum dimension of less than 500 nanometers.

19. The composition of claim 18, wherein the particle consists of a metal carbonate outer shell around a metal core.

20. The composition of claim 18, wherein the metal carbonate is uniformly dispersed throughout the particle.

21. The composition of claim 19, wherein the composition is a cream, a nanodispersion, a solution, a foam, a gel, a lotion, a paste, an ointment, a spray, a drop, or a suppository.

* * * * *

UNITED STATES PATENT AND TRADEMARK OFFICE
CERTIFICATE OF CORRECTION

PATENT NO. : 8,865,227 B2
APPLICATION NO. : 12/333585
DATED : October 21, 2014
INVENTOR(S) : Nicholas Dunwoody and Zachary S. Wilson It is certified that error appears in the above-identified patent and that said Letters Patent is hereby corrected as shown below:

On the Title Page,

Page 2, Column 2, Line 13 (under item (56), Other Publications):
Delete "Iontophoric" and insert -- Iontophoretic -- therefor.

Page 2, Column 2, Line 13 (under item (56), Other Publications):
Delete "in of" and insert -- of -- therefor.

Page 2, Column 2, Line 27 (under item (56), Other Publications):
Delete "Sterlization" and insert -- Sterilization -- therefor.

Page 2, Column 2, Line 40 (under item (56), Other Publications):
Delete "Nanbiotechnology" and insert -- Nanobiotechnology -- therefor.

Page 2, Column 2, Line 42 (under item (56), Other Publications):
Delete "Impared" and insert -- Impaired -- therefor.

Page 3, Column 2, Line 9 (under item (56), Other Publications):
Delete ""Nanocrystallne" and insert -- Nanocrystalline -- therefor.

In the Specification,

Column 9, Line 48:
Delete "*dfficile*" and insert -- *difficile* -- therefor.

Signed and Sealed this
Seventh Day of April, 2015

Michelle K. Lee
*Director of the United States Patent and Trademark Office*

CERTIFICATE OF CORRECTION (continued)
U.S. Pat. No. 8,865,227 B2

Column 10, Line 14:

Delete "integament" and insert -- integument -- therefor.

Column 13, Line 50:

Delete "vaccuum" and insert -- vacuum -- therefor.

Column 14, Line 65:

Delete "(typically 1-2 ppm)" and insert -- (typically ~ 1-2 ppm) -- therefor.

Column 14, Line 66:

Delete "(Aspergillusfumigatus)" and insert -- (Aspergillus fumigatus) -- therefor.

Column 15, Line 47:

Delete "Kriskal-Wallis" and insert -- Kruskal-Wallis -- therefor.